United States Patent [19]

Bonnet et al.

[11] Patent Number: 4,486,680
[45] Date of Patent: Dec. 4, 1984

[54] ULTRASONIC PIEZOELECTRIC DISINTEGRATER

[75] Inventors: Ludwig Bonnet, Knittlingen; Ehrenfried Bitrolf, Bretten-Ruit, both of Fed. Rep. of Germany

[73] Assignee: Richard Wolf GmbH, Knittlingen, Fed. Rep. of Germany

[21] Appl. No.: 472,010

[22] Filed: Mar. 4, 1983

[30] Foreign Application Priority Data

Mar. 4, 1982 [DE] Fed. Rep. of Germany ... 8205957[U]

[51] Int. Cl.³ .................. H01L 41/08; A61B 17/00
[52] U.S. Cl. ..................................... 310/323; 128/328
[58] Field of Search ............ 310/323, 325; 128/24 A, 128/24 R, 24.2, 32, 44, 67, 305, 328; 604/22

[56] References Cited

U.S. PATENT DOCUMENTS 4,046,150 9/1977 Schwartz et al. ................ 128/328
4,347,846 9/1982 Dormia .......................... 128/328

FOREIGN PATENT DOCUMENTS 2020345 11/1971 Fed. Rep. of Germany ...... 128/328
2428319 1/1976 Fed. Rep. of Germany ...... 128/328
227513 2/1969 U.S.S.R. ........................ 128/328
278958 8/1970 U.S.S.R. ........................ 128/328

Primary Examiner—Mark O. Budd
Attorney, Agent, or Firm—Hill, Van Santen, Steadman & Simpson

[57] ABSTRACT

This invention relates to piezoelectric transducers for generating ultrasonic oscillations having an end fitting joined to a distal metal element of a transducer which is connected to a wire emerging in the form of a loop structure. The invention consists in that the loop structure receiving the stone which is to be broken up comprises several wire strands forming a basket, which are coupled together at the extremities of the basket by means of tubular coupling elements and extent to the end fitting in twisted form.

8 Claims, 1 Drawing Figure

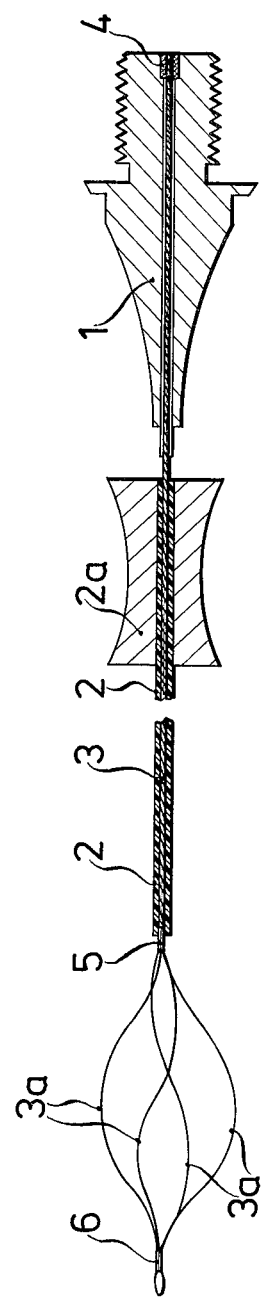

ULTRASONIC PIEZOELECTRIC DISINTEGRATER

BACKGROUND OF THE INVENTION

The present invention relates to piezoelectric transducers for generating ultrasonic oscillations for disintegrating bladder, urethra and kidney stones, of the kind which comprise two piezoelectric discs clamped between two metal elements and of which the metal element at the distal side has screwed into it an end fitting to which is connected a wire for transmitting the ultrasonic oscillations, passing through a plastics material sheath connected to the end fitting and having a basket-like loop structure projecting distally out of the sheath.

In the case of the aforesaid known piezoelectric transducers, the plastics material sheath connected to the end fitting is traversed by a single wire only, acting as a transmission element for the ultrasonic oscillation, as described in German Patent Specification No. DE-PS 20 20 345, for example. It is known moreover that a wire may be connected at the distal end projecting out of the sheath to a basket-like loop structure (Dormia loop structure), which serves the purpose of receiving a stone which is to be removed. The combination in accordance with the prior art referred to, in conjunction with an ultrasonic transducer, is not completely successful because this system tends to fracture easily on the one hand due to inadequate strength, and on the other hand because the efficiency of the ultrasonic oscillations for destroying the stones is very low, since the transverse oscillations required to this end cannot be transmitted.

It is an object of the invention to provide a transducer in which the transmission element extends from the end fitting to the loop structure in morphologically stable form and to obtain greater durability by reducing the risk of fracture, as well as a high efficiency during transmission of longitudinal and transverse oscillations to the stone.

SUMMARY OF THE INVENTION

Accordingly, in a piezoelectric transducer of the kind hereinabove referred to the loop structure comprises several and advantageously four, strands forming a basket by being outwardly bowed, said strands being joined together at the basket extremities by tubular elements and trasverse the surrounding sheath towards the end fitting in twisted form.

A morphologically stable but nevertheless flexible transmission element of high efficiency is obtained by means of this solution, a risk of fracturing also being largely eliminated. The individual strands are now continued at the proximal end of the loop structure, through the plastics material sheath. Due to the utilisation of tubular coupling elements for joining the individual strands at the ends of the loop structure, a strong joint is formed, which is obtained by brazing performed advantageously only in the central part of the tubular coupling elements, to prevent annealing and thus a reduction of the elastic deformability.

BRIEF DESCRIPTION OF THE DRAWING

In order that the invention may be more clearly understood reference will now be made to the accompanying drawing in which a transmission element for ultrasonic oscillations is illustrated in longitudinal cross-section without the connection to a piezoelectric transducer which per se is of known nature.

DETAILED DESCRIPTION OF THE PREFERRED EMBODIMENT

Reference now to the drawing there is shown a transmission element which comprises a known end fitting 1, the free end of which is screwed into the distal-side metal element of a piezoelectric transducer known per se and therefore not illustrated. This end fitting 1 has joined to it a plastics material sheath 2, for example a sheath of "Teflon" (Trade Mark), having a handle or grip 2a firmly joined to the plastics material thereof and axially displaceable for opening and closing the basket as will be described hereinunder.

The end fitting 1 and the sheath 2 are traversed by several and advantageously four twisted metal strands 3 one extremity of which is immobilised at 4 within the end fitting 1 by brazing. The twisted strands 3 are joined together at the distal extremity of the casing 2 by means of a tubular coupling element 5 and then led outwards in separate strands 3a which are outwardly bowed so as to form a basket for reception of a stone which is to be broken up, and again joined together at the distal extremity by means of a tubular coupling element 6.

The strands 3a are joined together by brazing only in the central portion of the tubular coupling elements 5 and 6, so that a reduction of the elastic deformability by annealing is eliminated as far as possible.

We claim:

1. A biological stone disintegrator of the type having a wire basket projecting from the distal end of an insertion sheath with means to oscillate the basket, comprising: a metal fitting member having a bore therethrough with a multi-wire strand having a proximal end secured to the fitting member extending longitudinally of the bore and projecting beyond the distal end of the fitting, a plastic insertion sheath received around the strand beyond the distal end of the fitting having a bore therethrough in which the strand extends, the strand projectable beyond a distal end of the sheath and forming a basket-like loop structure beyond the distal end of the sheath, the strand formed of a plurality of individual wires twisted together, the wires being outwardly bowed to form the loop structure, the wires connected together by tubular coupling means at a proximal end and at a distal end of the loop structure, the strand wires being twisted about each other substantially from the proximal end of the loop structure to the proximal end of the fitting member and means including the fitting member for imparting an ultrasonic vibration directly to the strand to cause the wires of the loop structure to vibrate to impart crushing vibrations to the loop structure.

2. A stone disintegrator according to claim 1 wherein the wires of the strand are coupled together and to the fitting member adjacent the proximal end of the fitting member.

3. A stone disintegrator according to claim 2, wherein there are four wires in the wire strand and loop structure.

4. A device for disintegrating bladder, urethra and kidney stones of the type having piezoelectric transducer means operatively connected to a wire, which comprises a device having a multi-wire strand which passes through a bore in an end fitting, said end fitting including a proximal end and a distal end, the end fitting adapted to be attached to a piezoelectric transducer means adjacent the proximal end of the end fitting, a plastics material sheath member having distal and proximal ends, the wire strand passing through said sheath member and being projectable from the distal end thereof, the wire strand terminating in a loop basket formed from the wires of the strand, the loop basket being defined at proximal and distal ends thereof by tubular coupling elements effective to couple the wires of the strand together at the proximal and distal ends of the loop basket, the plastics material sheath having means for movement of the sheath relative to the wire strand to cause said basket loop to open and close, the end fitting being directly connected to the wire strand and operable to transmit longitudinal and transverse ultrasonic vibrations from the piezoelectric transducer means through the wire strand to the basket for disintegration of stones trapped in the basket loop by the vibrations of the wires.

5. In a device for disintegrating bladder, urethra and kidney stones which comprises an end fitting to which is connected a wire for directly transmitting ultrasonic oscillations, means for associating the end fitting with an ultrasonic generator, the wire passing through a plastics material sheath extending beyond the end fitting, the wire comprising a multiwire strand having a distal end forming a loop basket structure with means joining the wires of the strand together at distal and proximal ends of the loop basket, the strand wires from the proximal end of the loop basket to a point of fixment of the strand to the end fitting being twisted together, the sheath movable with respect to the strand and effective to cause the basket loop to open and close, and the end fitting being effective to pass ultrasonic oscillations both longitudinally and transversely to the strand whereby the wires forming the basket loop are ultrasonicly oscillated for crushing stones entrapped therein.

6. A device according to claim 5 wherein the wires of the strand are connected together only at the proximal extremity of the end fitting and by means of tubular coupling elements centrally braised to the wire at the distal and proximal ends of the loop basket.

7. A device according to claim 6 wherein there are four wires to the strand.

8. A device according to claim 4 wherein there are four wires to the strand.

* * * * *